United States Patent
Goldberg (12)

(10) Patent No.: US 6,371,985 B1
(45) Date of Patent: Apr. 16, 2002

(54) PROSTHESES RESTRAINED BY IMMEDIATE ATTACHMENT WHILE INGROWTH PROCEEDS NATURALLY OVER TIME

(76) Inventor: Robert S. Goldberg, 1250 N. Dearborn St., #5A, Chicago, IL (US) 60610

( * ) Notice: Subject to any disclaimer, the term of this patent is extended or adjusted under 35 U.S.C. 154(b) by 0 days.

(21) Appl. No.: 09/459,283

(22) Filed: Dec. 17, 1999

Related U.S. Application Data

(63) Continuation-in-part of application No. 08/871,343, filed on Jun. 9, 1997, now Pat. No. 5,888,203, and a continuation-in-part of application No. 08/401,448, filed on Mar. 9, 1995, now Pat. No. 5,702,468.

(51) Int. Cl.[7] .................................................. A61F 2/28
(52) U.S. Cl. .................. 623/16.11; 623/13.11; 623/23.57
(58) Field of Search ........................... 623/13.17, 13.18, 623/16.11, 17.11, 21.12, 21.14, 23.11, 23.12, 23.13, 23.14, 22.32, 22.33, 13.11, 23.57

(56) References Cited

U.S. PATENT DOCUMENTS

| | | | | |
|---|---|---|---|---|
| 3,593,342 A | * | 7/1971 | Niebauer | 623/23 |
| 3,745,590 A | * | 7/1973 | Stubstad | 623/23 |
| 3,973,277 A | * | 8/1976 | Semple | 623/23 |
| 4,149,277 A | * | 4/1979 | Bokros | 623/22 |
| 4,450,591 A | * | 5/1984 | Rappaport | 623/23 |
| 5,156,625 A | * | 10/1992 | Marchetti | 623/22 |
| 5,376,126 A | * | 12/1994 | Lin | 623/23 |
| 5,797,916 A | * | 8/1998 | McDowell | 606/74 |

* cited by examiner

Primary Examiner—Michael J. Milano
(74) Attorney, Agent, or Firm—Michael Best & Friedrich, LLC

(57) ABSTRACT

The invention is a surgically implantable bone and bone joint prosthesis which is designed to be directly attached during surgery and which includes ingrowth receptive zones or stationing sites for delayed ingrowth adhesion naturally over time. The ingrowth receptive zones preferably emulate cancellous bone and are at locations on the body member corresponding generally to the area where connective tissue naturally attaches in vivo.

42 Claims, 6 Drawing Sheets

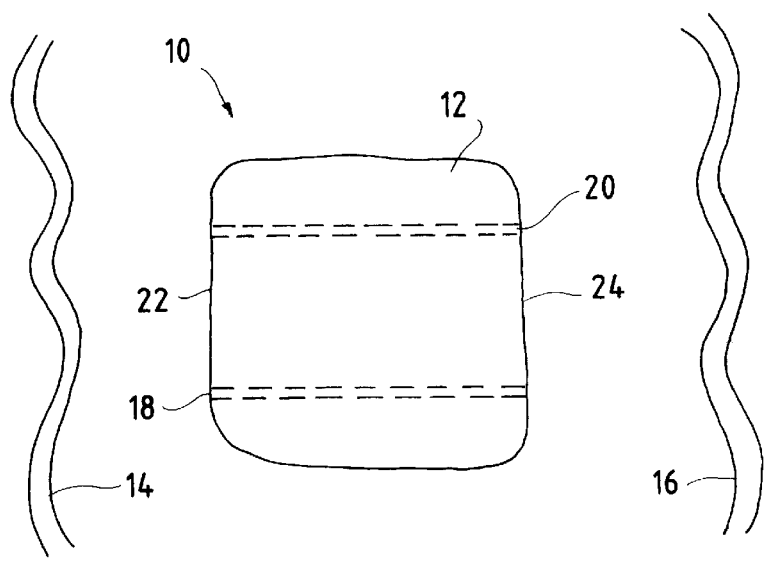
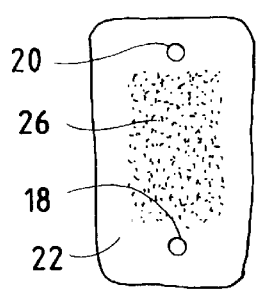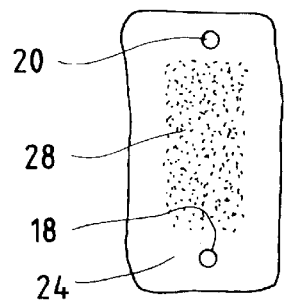
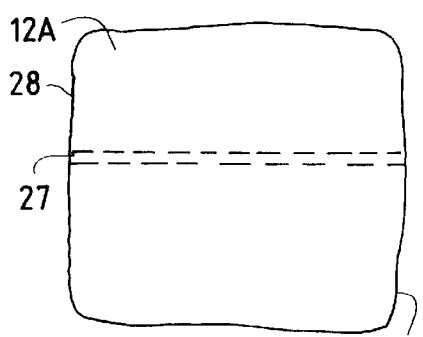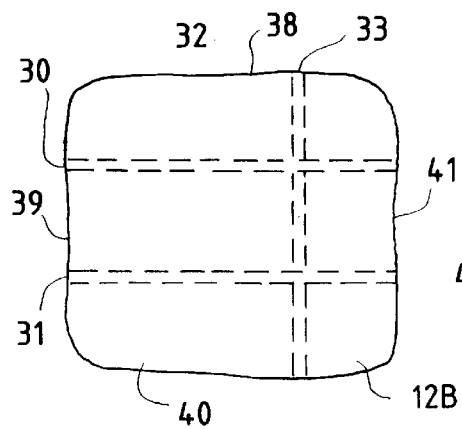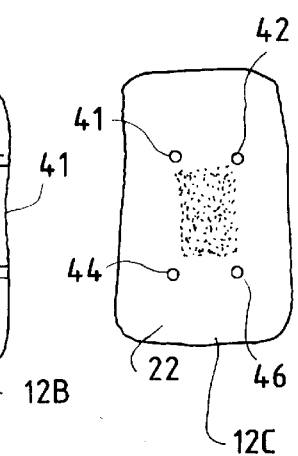

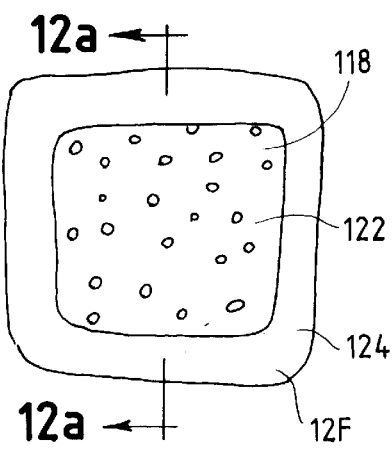
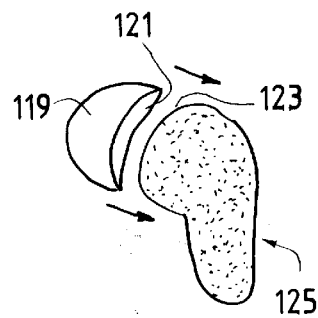
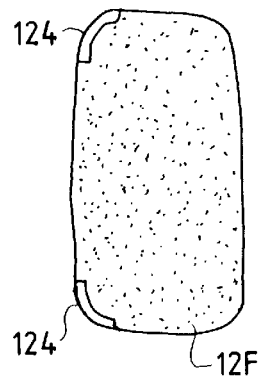
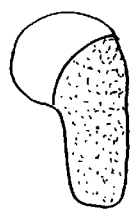
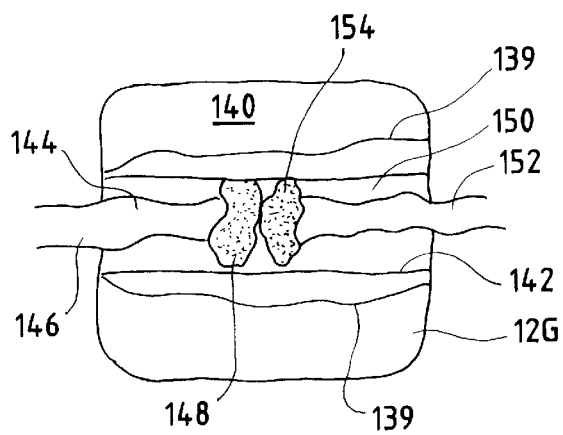
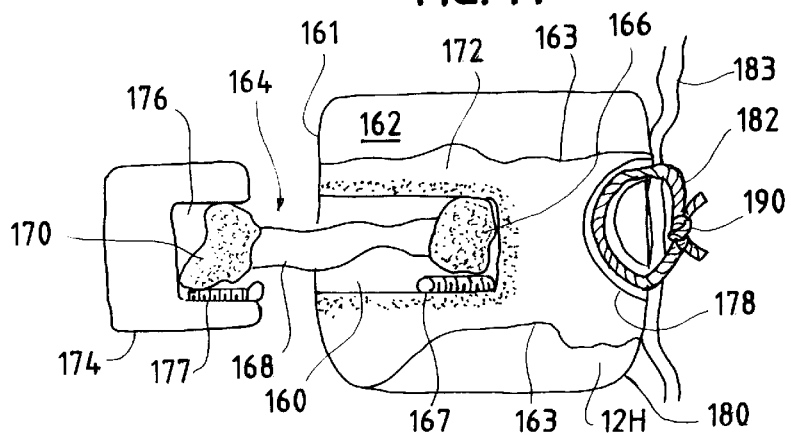

PROSTHESES RESTRAINED BY IMMEDIATE ATTACHMENT WHILE INGROWTH PROCEEDS NATURALLY OVER TIME

This is a continuation-in-part of application Ser. No. 08/871,343 filed Jun. 9, 1997, which issued as U.S. Pat. No. 5,888,203 on Mar. 30, 1999, and is in turn a continuation-in-part of application Ser. No. 08/401,448 filed Mar. 9, 1995, which issued as U.S. Pat. No. 5,702,468 on Dec. 30, 1997.

FIELD OF THE INVENTION

This invention relates to prostheses. More particularly, this invention relates to new prostheses and methods for safely and effectively restraining such prostheses using a combination of direct immediate attachment to stabilize the prostheses while attachment to native connective tissue by ingrowth to the prostheses proceeds naturally over time.

BACKGROUND OF THE INVENTION

Implants or prostheses are employed for restoring damaged upper and lower extremity bones such as fingers, wrists, elbows, knees and ankles of human patients. These prostheses are especially useful in the reconstruction of joints which, for example, have been damaged by pathological conditions such as rheumatoid arthritis, degenerative arthritis, aseptic necrosis, and for treating trauma which may have a debilitating effect on articular joints.

Extra articular bone segment replacement includes long bones replaced after destruction processes, such as trauma and tumors. For example, if a segment of femur (thigh) or radius (forearm) bone shafts is being destroyed by malignant tumor, it may be replaced by a transplanted cadaver bone graft of that segment. Native tendons with connected muscles may be reattached to that bone graft to preserve the function of limb motion. Similarly, a synthetic bone replacement, such as one made of ceramic or metal, could be used to replace those segments.

Unfortunately, some joint implant designs available currently or described in the past have drawbacks arising from their construction and design. For example, current and past scaphoid and lunate carpal bone replacements generally cannot reproduce the normal and vital kinematics of that joint, normally dictated by native ligamentous restraints.

Joint replacement designs or arthroplasties which rely solely on man-made mechanical restraint mechanisms of various types (e.g. semi-constrained elbow arthroplasties), also may fail to properly simulate or replace native ligamentous and capsular restraints. Many arthroplasties also attempt to change the native biomechanical properties of the replaced joint instead of reproducing the native properties. New prostheses which restore native biomechanical properties are discussed and claimed in the present inventor's U.S. Pat. Nos. 5,702,468 and 5,888,203, which are incorporated by reference.

There are three types of arthroplasties: 1) unconstrained, 2) semi-constrained and 3) fully constrained. A common flaw with all of these current joint replacement designs is the inability to reconstruct and re-attach the replaced joint's vital native capsular and ligamentous restraints, which dictate, in large measure, the behavior and stability of the joint (i.e., its kinematics).

The present invention may apply to any synovial or diarthroidial human joint, or to extra-articular bone segment replacement. One preferred application of the invention is to joints whose motion and stability are both quantitatively and qualitatively significant and therefore functionally important.

The definitions of "joints" and "articulations", adopted from Stedman's Medical Dictionary, 1982, pp. 126–7 and p. 737, refer to three types of "articulations": fibrous, cartilaginous, and synovial. The synovial articulation is the preferred application of this invention. A synovial articulation (or diarthrodial joint) is a joint allowing various amounts and types of motion in which the bony surfaces are covered with a layer of hyaline or fibrous cartilage. There is a joint cavity containing synovial fluid and lined with a synovial membrane, reinforced by a fibrous capsule and by ligaments.

In order to better explain the vital importance of the natural capsular and ligamentous restraints in a synovial joint, and to illustrate the shortcomings of arthroplasties which do not reconstruct these native restraints, replacement of wrist carpal bones will be discussed below. This discussion will illustrate the anatomy, function and kinematics of the carpus with an emphasis on demonstrating the necessity and unique contribution of the invention as it applies to replacing the scaphoid and lunate carpal bones. This invention, however, is not limited to scaphoid and lunate prostheses but rather extends to all upper and lower extremity arthroplasties in any synovial or diarthroidial joints which are functionally important, as well as to extra-articular bone segment replacement.

Wrist movement is apportioned between the radiocarpal and midcarpal joints in a very complex manner. Accordingly, it is essential that a carpal implant be restrained in a manner as close as possible to that achieved with the native carpal bones and native capsule and ligaments in order to maintain the normal kinematics of the carpus. This serves to preserve the shape of the implant and to prevent wear, fracture, dislocation and particulate synovitis.

To date, a satisfactory technique for reconstruction of native restraints (capsule, ligament and tendon) with arthroplasties has not been achieved. The present invention is uniquely designed to allow the surgeon to accurately and predictably replace native connective tissue restraints and thus prevent the above-mentioned causes of failure.

Accordingly, an object of the present invention is to provide an improved method and prostheses for replacing upper or lower extremity bone(s) in a joint of a human.

A further object of the present invention is to provide an improved method and prostheses for replacing extra-articular bone segments, that is, segments of bones outside of human bone joints.

It is another object of the present invention to provide prostheses for replacing upper or lower extremity bone(s) of a joint in which the prostheses are further restrained using ingrown native ligament, capsule, and tendon.

It is yet another object of the present invention to provide prostheses for replacing upper or lower extremity bone joints as well as extra-articular bone segments in which the reconstruction of native connective tissue restraints encourages normal joint global kinematics, and tendon-muscle function, respectively.

It is a further object of the present invention to provide a method and prostheses for replacing upper or lower extremity bone joints as well as extra-articular bone segments by direct immediate attachment to ligament, capsule, bone, or tendon adjacent the bone or portion of which is to be replaced by the prosthesis while ingrowth adhesion from native ligament, capsule, or tendon to discrete ingrowth receptive zones of the prosthesis proceeds naturally over time, preferably with substantial vascularized tissue ingrowth at the ingrowth receptive zones.

These and other objects and advantages of the invention will appear hereinafter.

SUMMARY OF THE INVENTION

The present invention accomplishes the foregoing objects by providing a surgically implantable bone prosthesis including a body member, means for direct immediate attachment of the body member, and at least one ingrowth receptive stationing site on and/or within the body member for delayed ingrowth adhesion naturally over time. The direct immediate attachment of the body member as well as the ingrowth which proceeds over time is to adjacent native connective tissue (ligament, capsule or tendon).

The body member is made totally or partially from any appropriate material including but not limited to a biocompatible, medically inert material such as ceramic, titanium, a stainless steel alloy, a non-ceramic substrate with a ceramic or other biocompatible, medically inert coating, or an open-celled lattice tantalum metal-carbon foam composite material. The body member may comprise a single component or body member as illustrated in FIGS. 1–15a, or it may be made up of at least two components or body members (e.g. FIGS. 16–18) contoured to resemble the shape of a bone, bones or a portion of a bone or bones which are to be replaced by the prosthesis.

In order to achieve the desired tissue ingrowth over time, the body member must be buttressed and affixed to adjacent connective tissue. Mooring means are provided to draw connective tissue to the ingrowth surface of the stationing site achieving the desired buttressing/affixation. Furthermore, adhesive with impregnated bone or connective tissue ingrowth factors could be used to add strength for temporary holding power as tissue ingrowth progresses over time. The greater the contact area of connective tissue to the implant ingrowth surface of the stationing site, the greater the effectiveness of the natural tissue ingrowth over time. The mooring means preferably significantly reduce relative motion between the implant and/or the adjacent connective tissue and bone, further promoting stable progressive biologic ingrowth over time.

Conventional sutures, anchors, interference screws, medical staples or other external mooring means may serve as mooring means to buttress and affix the body member to adjacent connective tissue or bone. Alternatively, the mooring means can be ligamentous means, which are natural or artificial, and porous or non-porous, including but not limited to local tissue, autografts, allografts, xenografts and synthetic grafts. In one preferred embodiment, the ligamentous means may be a porous woven fabic which is tissue ingrowth receptive. In another preferred embodiment, ligamentous means in the form of natural tissue such as capsular strips, bone-ligament-bone graft, or tendon, may be used. When bone-ligament-bone grafts are used, the volume of the bone portions of the bone-ligament-bone grafts may be enhanced with synthetic bone pastes such as Norian®. When suture or ligamentous means are used, the suture or ligamentous means preferably are affixed to adjacent native ligament or capsule, or to the surrounding native cancellous bone itself to achieve the buttressing/affixation to the ingrowth surface of the stationing site. Sutures, interference screws or adhesive (including inert and biologic adhesives) can be used to affix ligamentous means to adjacent native ligament or capsule or to the surrounding native cancellous bone.

The stationing sites preferably will emulate cancellous bone and will be at locations on the body member corresponding generally to the areas where connective tissue naturally attaches in vivo to bones or portions of bones which are to be replaced by the prosthesis. Additionally, the stationing sites preferably will be of a size and shape corresponding generally to the size and shape of the metaphyseal or diaphyseal areas of bone to which the connective tissue is attached in vivo to the bones or portions of bones which are to be replaced by the prosthesis.

The stationing sites may be treated with humeral growth factors to further tissue induce ingrowth. In addition to the bone and connective tissue ingrowth factors, the stationing sites may be treated with biologic adhesives such as fibrin glue to improve the hold of the mooring means.

In one preferred embodiment, at least one body member of the prosthesis includes a pair of generally parallel channels through which the mooring means can be passed to draw connective tissue to the ingrowth surface stationing site adjacent to the channel openings. In another preferred embodiment, at least one body member includes a channel which loops into and back out of the surface of the body member and the mooring means is passed through this looping channel to draw connective tissue to the ingrowth surface stationing site adjacent to the channel openings. The mooring means used may be conventional suture or ligamentous means as described above.

When mooring means in the form of ligamentous means or suture are passed through channels in a body member to buttress/affix the body member to adjacent connective tissue or bone, such mooring means (which preferably are not attached to the channels before implantation) moor the body member but allow it controlled translational gliding motion (by virtue of elasticity if the attached connective tissue) emulating at least some of the native kinematics of the bone or bones being replaced. The resulting tethering and suspension of the body member prevents undesired excessive motion of the implant and thereby maintains the positional relationship of its ingrowth surface(s) to attached connective tissue. This stabilization encourages undisturbed ingrowth of attached native connective tissue into the stationing sites to proceed naturally over time.

In a still further embodiment of the invention, mooring means in the form of ligamentous means or suture may be physically anchored in one or more channels. This may be achieved by physically attaching the suture or ligamentous means to the channel wall (e.g., by adhesive, anchors, interference screws, etc.). It may also be achieved—over time—using ligamentous means and providing ingrowth receptive zones on the walls of the channel (an example of ingrowth surfaces within the body member), so that attachment by ingrowth proceeds while the ligamentous means are anchored to the channel ingrowth surface using the above-mentioned means of anchoring (e.g.; interference screws).

Alternatively, one bone end of each of a pair of bone-ligament-bone grafts can be anchored in the channels with permanent or dissolving interference screws or anchors, and/or with adhesive. In this case, it is preferred that the anchored bone of two grafts at opposite ends of a channel will touch. Over time, the touching ends of both bone-ligament-bone grafts will grow together producing a single bone-ligament-bone-ligament-bone ligamentous means mooring the body member. Indeed, if ingrowth surfaces are made available in the channel, this complex of bone-ligament-bone-ligament-bone ligamentous means will over time itself adhere and grow into the channel ingrowth surface, adding to the anchorage and stability of the implant.

In another embodiment of the invention, the mooring means may be secured to the periphery of the body member. When mooring means in the form of ligamentous means or suture are used, securement may be by way of eyelets in the surface of the body member, by way of permanent or dissolving interference screws or anchors, with the use of adhesive, by molding the ligamentous means (or suture) in place during formation of the body member, or by other means. When mooring means in the form of ligamentous means are used, the ligamentous means also may be secured to the periphery of the body member with a biologic adhesive such as fibrin glue, with or without connective tissue ingrowth factors.

The body member may be stabilized as explained in my U.S. Pat. Nos. 5,702,468 and 5,888,203, by suspending it on ligamentous means or suture along at least two crisscrossing, preferably substantially perpendicular axes, thereby further restraining the body member to limit translation and destructive shear of the implant short term while permitting limited necessary movement of the body member (e.g., rotation of scaphoid implant) in relation to adjacent bones as ingrowth proceeds from the connective tissue to the stationing sites, naturally over time.

The above, as well as other objects and advantages of the invention, will become apparent from the following detailed description of the preferred embodiments as illustrated in the accompanying drawings.

BRIEF DESCRIPTION OF THE DRAWINGS

FIG. 1 is a diagrammatic/symbolic representation of a surgically implantable prosthesis in accordance with the present invention;

FIGS. 1a and 1b are side views of the surgically implantable prosthesis of FIG. 1;

FIG. 2 is a diagrammatic/symbolic representation of an alternative embodiment of a surgically implantable prosthesis in accordance with the present invention;

FIG. 3 is a diagrammatic/symbolic representation of another alternative embodiment of a surgically implantable prosthesis in accordance with the present invention;

FIG. 4 is a diagrammatic/symbolic representation of a further alternative embodiment of a surgically implantable prosthesis in accordance with the present invention;

FIG. 1a is a cross-sectional view of the surgically implantable prosthesis of FIG. 11 taken along lines 11a—11a in FIG. 11;

FIG. 12 is a further alternative embodiment of a surgically implantable prosthesis in accordance with the present invention in which an entire body member is canalicularized;

FIG. 12a is a cross-sectional view of the prosthesis of FIG. 12, taken along lines of 12a—12a of FIG. 12;

FIGS. 12b and 12c are illustrations of a smooth surface cap applied to a fully canalicularized body member;

FIG. 13 is yet another diagrammatic/symbolic representation of an embodiment of the present invention in which bone-ligament-bone grafts are fixed within a channel in a surgically implantable prosthesis;

FIG. 14 is a diagrammatic/symbolic representation of a surgically implantable prosthesis in accordance with the present invention in which a bone-ligament-bone graft is used to moor the prosthesis to adjacent bone;

DETAILED DESCRIPTION OF THE INVENTION

Figure 5:
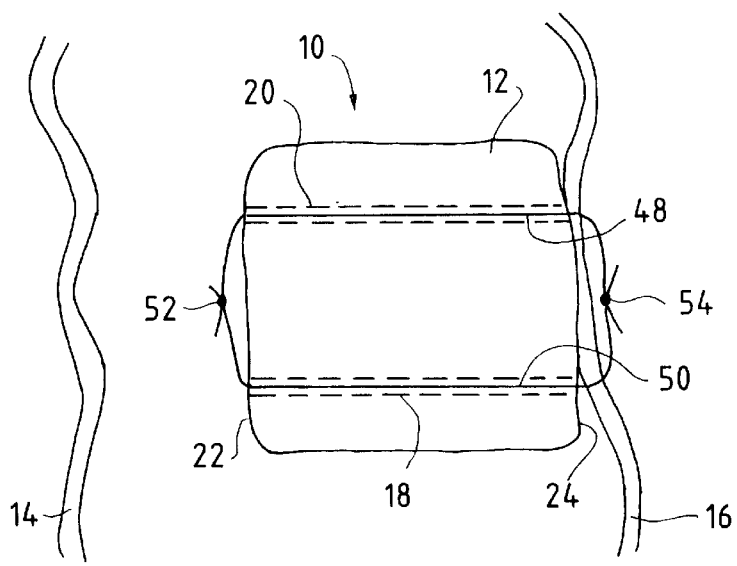
FIG. 5 is a top view of the prosthesis of FIG. 1 representing mooring and buttressing to capsule on one side of the prosthesis.

The examples of lunate and scaphoid carpal bone prostheses described in my U.S. Pat. Nos. 5,702,468 and 5,888,203 are incorporated by reference. In accordance with the present invention, the prostheses described in those patents may be provided with means for direct immediate attachment and at least one ingrowth receptive zone or stationing site accessible on or in the body member for delayed ingrowth adhesion naturally over time to native connective tissue. One skilled in the art will readily discern from these examples in my prior patents, that similar prostheses and methods for safely and effectively performing upper and lower extremity arthroplasties generally may likewise be provided with means for direct immediate attachment to native connective tissue or bone adjacent the bone or portion of the bone which is to be replaced by the prosthesis and at least one ingrowth receptive zone stationing site accessible on or beneath the surface of the body member for delayed ingrowth adhesion naturally over time to native connective tissue.

Although each human joint has its own unique shape and kinematic properties, the principles of the present invention are applicable to any synovial or diarthroidial joint as well as to extra-articular bone segment replacements. The principles and implementation of the present invention are illustrated diagrammatically and symbolically in the following FIGS. 1–15a and 18 and by specific reference to the joint treated in FIGS. 16 and 17.

Turning first to FIGS. 1, 1a and 1b, a surgically implantable prosthesis 10 comprising a single body member 12 in accordance with the present invention is shown before implantation, between connective tissue (capsule) portions 14 and 16 of a synovial or diarthoidal human joint. The joint may be, for example, a scapho-lunate or a luno-triquetral joint, with the body member 12 symbolically representing the lunate bone. Connective tissue portions 14 and 16 in this example are portions of palmer and dorsal wrist capsule. In the embodiment illustrated, body member 12 may be made from ceramic, titanium, a stainless steel alloy, or a non-ceramic substrate with a ceramic or other bio-compatible, medically inert coating. A pair of generally parallel channels 18 and 20 pass through body member 12. As explained below, mooring means extend through these channels to buttress and affix the body member to the adjacent connective tissue.

Capsule portions 14 and 16 are adjacent, respectively, to surfaces 22 and 24 of the body member. As seen in the side views of FIGS. 1a and 1b, surfaces 22 and 24 include ingrowth receptive zones or stationing sites 26 and 28 for delayed ingrowth adhesion to the connective tissue portions naturally over time. These stationing sites 24 and 26 are intended to correspond diagramatically and symbolically to native non-articular anatomic surfaces where connective tissue naturally attaches in vivo. In all cases, the greater the surface contact area of connective tissue to the ingrowth surface of the stationing sites, the greater the opportunity for natural ingrowth over time. Stationing sites 20 and 28 optionally may be treated with humeral ingrowth factors to accelerate the ingrowth process.

Important medical science advancements are being made in the identification and use of native humeral growth factors to promote local growth and healing of bone and connective tissues (ligament, capsule and tendon). While not yet widely commercially available, these factors may be used to promote ingrowth of connective tissue into implant prostheses (joint replacements and segmental replacements) through, inter alia, chemotaxis, mitogenesis and cell differentiation. Examples of ingrowth factors include bone matrix proteins (e.g., osteocalcium, osteonectin, osteopontin), growth factors (e.g., transforming growth factor beta, insulin-like growth factor, interleukins and bone morphogenic proteins), and connective tissue ingrowth factors (e.g., platelet derived growth factor, fibroblastic growth factor, insulin growth factor and transforming growth factor-beta). Any of these may be used in the practice of the present invention as, for example, by treating the ingrowth surfaces of the stationing sites 20 and 28.

Buttressing and affixation of the body member to adjacent connective tissue can be accomplished using any number of mooring means (sutures, ligamentous means, etc.). For example, a single channel 27 may be present in the body member, as shown in FIG. 2 to accept suture or ligamentous means to buttress and affix connective tissue to one or both opposite sides 28 and 29 of body member 12A. Or, four crisscrossing, non-intersecting channels 30, 31, 32 and 33, can be used as in FIG. 3, to draw connective tissue to up to four sides 38, 39, 40 and 41 of body member 12B. In yet another alternative, two pairs of generally parallel channels 41, 42, 44 and 46 may pass through a body member 12C as illustrated in the side view of the body member shown in FIG. 4.

Figure 6:
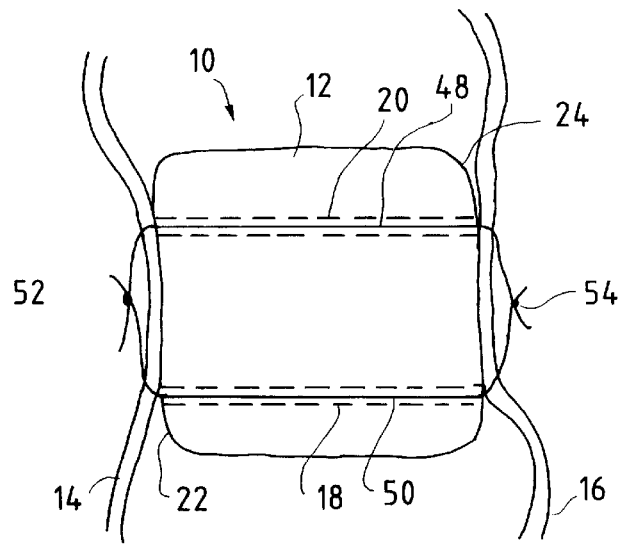
FIG. 6 is a top view of the prosthesis of FIG. 1 representing mooring and buttressing to capsule on two sides of the prosthesis.

In FIG. 5, capsule portion 16 has been drawn up against and buttressed and affixed to surface 24 of body member 12 by mooring means in the form of sutures 48 and 50 which are tied off at opposite ends at knots 52 and 54. Further buttressing/affixation is illustrated in FIG. 6 in which capsule portions 14 and 16 have been buttressed and affixed respectively to surfaces 22 and 24 of the body member again by mooring means in the form of sutures 48 and 50. In both cases, the sutures are used to draw the connective tissue up against stationing sites 26 and 28 to provide direct immediate affixation of body member 12 to the connective tissue. The mooring means also reduce relative motion between the prosthesis and adjacent connective tissue and bone (not shown), further promoting and ensuring stable, progressive biologic ingrowth over time. Also, the mooring means may be local tissue such as capsular strips, bone-ligament-bone graft, or tendon autografts, allografts, xenografts and synthetic grafts, such as porous woven fabric which is tissue ingrowth receptive. In the latter case, the channels will be appropriately-sized (typically enlarged) to permit such naturally larger ligamentous means to pass therethrough.

Figure 7:
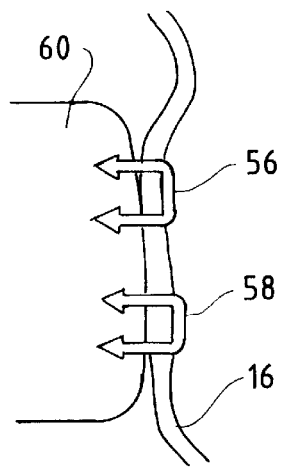
FIG. 7 is a representation of a portion of a prosthesis in accordance with the present invention, showing mooring of capsule to the prosthesis by way of surgical staples.

A like result may be obtained by using mooring means in the form of medical staples 56 and 58 applied to a body member 60 as shown in FIG. 7. Conventional anchors and interference screws or other external mooring means may be used here in a like manner to buttress and affix the connective tissue to the ingrowth receptive zones.

Figure 8:
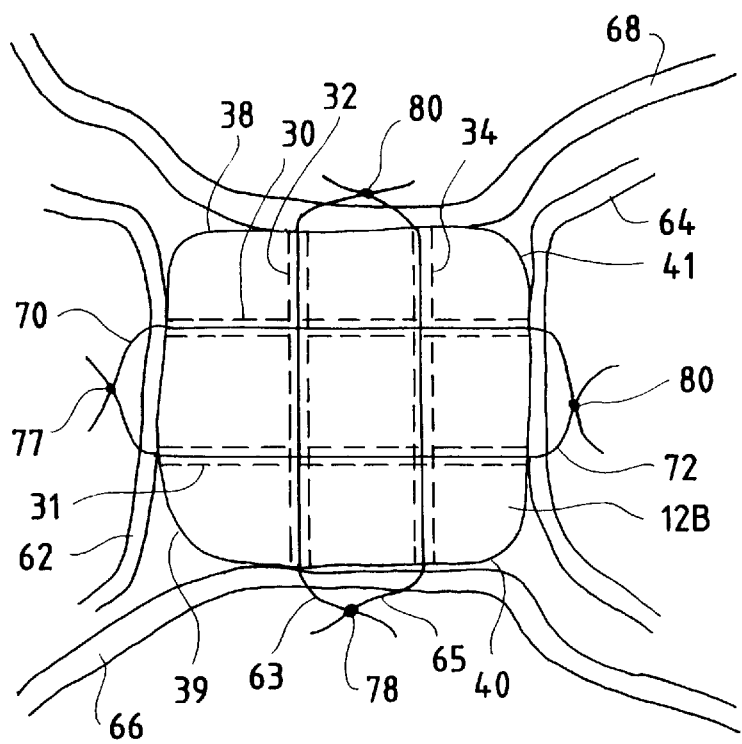
FIG. 8 is a representation of the surgically implantable prosthesis of FIG. 3 representing mooring and buttressing of capsule portions to four sides of the prosthesis.

FIG. 8 represents body member 12B of FIG. 3, with adjacent capsule portions 62 and 64 buttressed against sides 39 and 41 of the body member by way of suture 70 and 72 in channels 30 and 31 and tendons 66 and 68 buttressed against sides 38 and 40 using sutures 63 and 65 which pass through channels 32 and 34. The sutures are tied off at knots 77, 78, 79, and 80 to provide direct immediate attachment while ingrowth proceeds over time to stationing sites on sides 38, 39, 40 and 41.

Figure 8A:
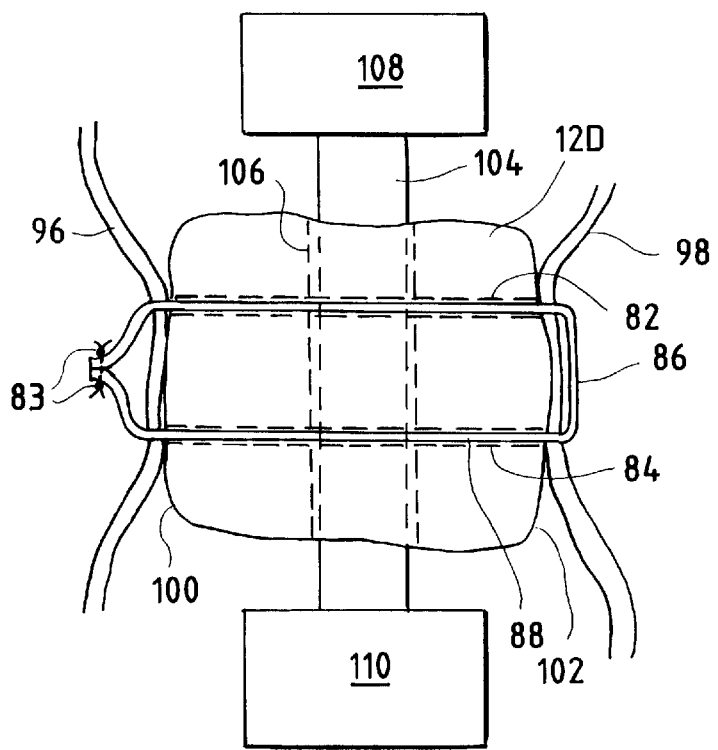
FIG. 8a is another representation of the surgically implantable prosthesis of FIG. showing mooring to capsule on two sides of the prosthesis by suture and suspension to surrounding bones and on the other two sides by a capsular strip.

FIG. 8a is a diagramatic/symbolic representation of a body member 12D in which capsule portions of 96 and 98 are buttressed against sides 100 and 102 of the body member by way of a single tendon ligamentous means 86 which runs through channels 82 and 84 as illustrated, and is tied off with a suture at knots 83. A capsular strip 104 passes through an enlarged channel 106, shown in part and for illustration purposes by cutting the body member away at 88. Channel 106 is generally perpendicular to channels 82 and 84. Channels 82 and 84 do not intersect in this example. Capsular strip 104, which is attached to adjacent bones 108 and 110 by conventional means such as anchors or staples (not shown), helps suspend the body member.

Figure 9:
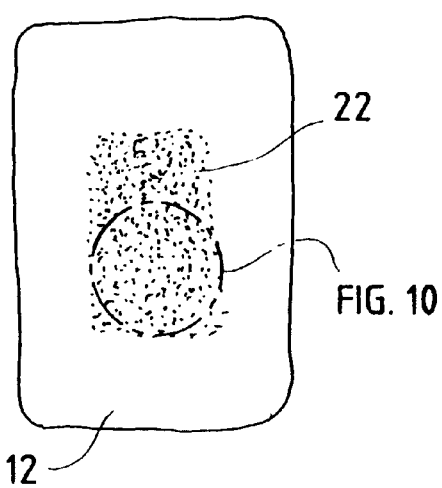
FIG. 9 is a diagrammatic/symbolic representation of an ingrowth receptive stationing site of the surgically implantable prosthesis of FIG. 1.
Figure 10:
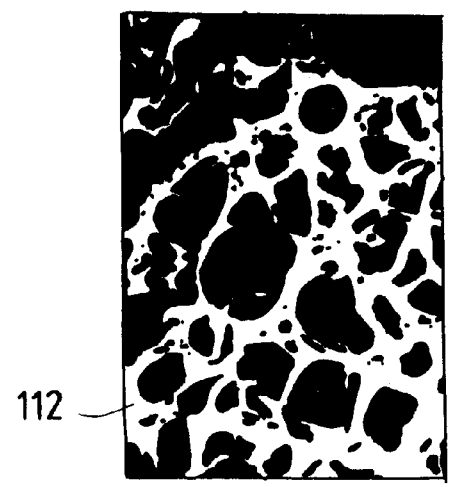
FIG. 10 is a greatly enlarged view of a portion of ingrowth surface of the surgically implantable prosthesis of FIG. 9.

FIG. 9 is a diagramatic/symbolic representation of ingrowth receptive zone 22 of body member 12 (FIGS. 1, 1a and 1b) in which material engineered with reticular canaliculi are distributed across the surface of the ingrowth receptive zone penetrating into the body member. FIG. 10 is a greatly enlarged representation of a portion of the ingrowth surface showing a reticular porous structure 112 of the type sought to be achieved (corresponding to areas of native bone to which native connective tissue is attached, in situ). As seen there, canaliculi forming interconnecting and crossing passages or channels extend into the body member emulating the reticular or lattice-like structure of cancellous bone into which the connective tissue will grow and anchor over time.

Figure 11:
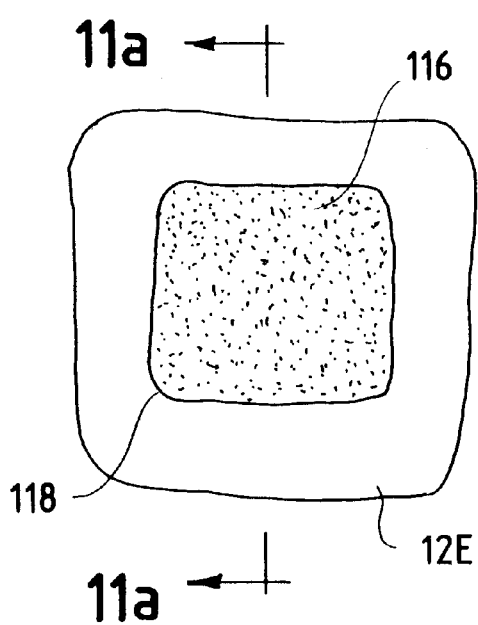
FIG. 11 is a top view of a surgically implantable prosthesis in accordance with the present invention with a canalicularized insert.
Figure 11A:
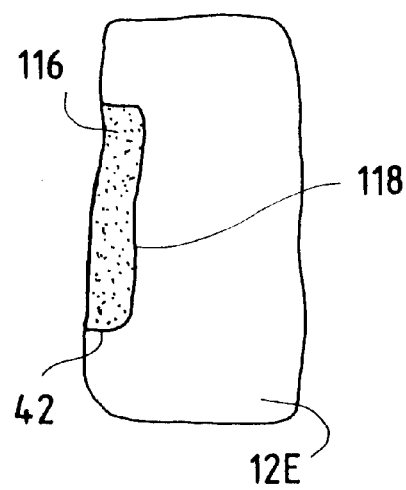

The ingrowth receptive zones may be formed in the body members by appropriately treating the selected ingrowth portions of body member surfaces either during formation of the body members or thereafter. Alternatively, as shown in FIG. 11 and its cross-sectional view in FIG. 11a, taken along line 11a—11a in FIG. 11, a synthetic canalicularized insert 116 may be fixed into a preferred cavity 118 in the surface of a body member 12E. Insert 116 may be made, for example, in accordance with the teaching of "Characterization of a New Porous Tantalum Biomaterial for Reconstructive Orthopedics", by J. D. Bobyn, Ph.D., S. A. Hacking, M. Eng., S. P. Chan, M.D., K-K Toh, M.D., J. J. Krygier, C.E.T., M. Tanzer, M.D., Jo Miller Orthopaedic Research Laboratory, Division of Orthopaedics, McGill University, Montreal, Quebec, Canada, which is a published document distributed in connection with a scientific exhibit at the 1999 Annual Meeting of the American Academy of Orthopaedic Surgeons, Anaheim, Calif. See also, "The Strength of Soft Tissue Attachment to Porous Tantalum" by S. A. Hacking, M. Eng., K-K Toh, M.D., J. D. Bobyn, Ph.D., M. Tanzer, M.D., and J. J. Krygier, C.E.T. presented at the 24th Annual Meeting of the Society for Biomaterials, Apr. 22–26, 1999, San Diego, Calif., USA.

In yet another alternative approach, as illustrated symbolically in FIGS. 12 and cross-sectional view 12a, the entire body member 12F is canalicularized as at 122—either on formation from a material like an open-celled lattice tantalum metal-carbon foam composite referred to in the above-noted references or by subsequent treatment—and then those areas 124 where ingrowth is not desired (i.e., articular surfaces of the implant) are sealed for example by coating or capping those areas to produce a smooth articular-like zone 124 adjacent the uncapped ingrowth areas. Thus, articular zone 124 may be hard and smooth and positioned to correspond to articular areas in the native bone being replaced by the prosthesis. These sealed or capped zones would be positioned to articulate within a joint against an opposing cartilage surface or against another joint replacement articular zone as illustrated in FIGS. 12b and 12c. Thus, in FIG. 12b, a smooth surfaced cap 119 with a cavity 121 shaped to receive the implant head 123 of a fully canalicularized artificial body and stem 125 is shown next to the implant head. In FIG. 12c, cap 119 is shown molded to head 123.

Other promising techniques for producing canalicularized ingrowth receptive zones and inserts are suggested in "Molecular Manipulation of Microstructures: Biomaterials, Ceramics, and Semiconductors" by Samuel I. Stupp and Paul V. Braun, *Science,* Vol. 277, Aug. 29, 1997 and "Organoapatite Growth on an Orthopedic Alloy Surface" by Samuel Stupp, Ph.D., et al. These articles describe techniques for synthetically generating apatite-based materials ("organoapatites") which can function as artificial bones. These organoapatites are synthesized by the nucleation and growth of hydroxyapatite material in aqueous solutions containing appropriate organic macromolecules. It is believed that this organic component can be used to produce an appropriate microstructure or canalicularized zone to promote connective tissue ingrowth. Such materials may also be treated to carry growth factors to promote ingrowth, as noted above. In one alternative approach, the body member (or the ingrowth insert) may be made from an open-celled lattice tantalum-carbon composite material such as Hedrocel® which is available from Implex Corporation. This material is a composite of reticulated vitreous carbon foam and tantalum metal. The composite is made by applying tantalum metal to a reticulated vitreous carbon foam construct in a chemical vapor infiltration process. These materials may also be treated to carry growth factors to promote ingrowth, as noted above.

Turning now to FIG. 13, the use of bone-ligament grafts to suspend, buttress, and affix prostheses in accordance with the invention is illustrated. In this figure, a body member 12G is shown, cut away at 139 on its top surface 140 to expose a channel 142 through the body member. A first ligamentous means in the form of a bone-ligament graft 144 is shown, with ligament portion 146 and bone portion 148. A second ligamentous means in the form of a bone-ligament graft 150 is shown with ligament portion 152 and bone portion 154. Bone-ligament grafts 146 and 154 preferably touch at 158 (which need not be at the center of the channel). Over time, the touching bones of the two bone-ligament grafts will grow together receiving blood supply by neovascularization from surrounding connective tissue and producing a single bone-ligament-bone-ligament ligamentous means mooring the body member in place. Ligaments 146 and 152 are attached to adjacent connective tissue and/or bone (not shown) to draw these tissues to the implant, buttressing and affixing body member 12F in the same fashion as described above.

Typically, a bone ligament-bone graft has bone fragments at either end, which when harvested may have inadequate size/volume of bone to be held well by even an interference screw. Therefore, to enhance the volume of the bone fragments at the ends of the graft, one could place those bone fragments within a volume of Norian® (or other) synthetic bone paste while it is in its "liquid" or soft stage and wait a short time (during surgery) for the paste to harden around and to the bone, creating a larger volume block to anchor that bone-ligament-bone, with, e.g., an interference screw either within the implant channel and/or, at the opposite end, to native bone.

FIG. 14 illustrates another way in which bone-ligament mooring means may be used. As shown in this figure, a body member 12H has a blind or partial depth channel 160 which opens onto side 161 of the body member and which is exposed for illustration purposes by cutting away at 163 a portion of the top surface 162 of the body member. A bone-ligament-bone graft 164 is shown with one bone end 166 anchored within the channel using an interference screw 167 which may bite into the wall of the channel or screw down on a preformed mating thread along the wall at the distal end of channel 160 to wedge bone end 166 in the channel. A ligament portion 168 extends partly out of the channel and a bone portion 170 is accessible for attachment to adjacent bone. In this case, channel 160 has been provided with an ingrowth surface 172. Thus, over time, ingrowth will proceed between bone 166 along surface 172. The second bone portion 170 will be anchored to an adjacent bone 174 by boring an appropriately-sized hole 176 to initially wedge bone portion 170 in place using interference screw 177, but which preferably will permanently anchor over time by bone-to-bone ingrowth. Body member 12H also includes a looping channel 178 opening onto its opposite side 180. Ligamentous means in the form of a xenograft 182 passes through channel 178 and is used to buttress and affix capsule 183 to an ingrowth receptive zone 184 as illustrated in FIG. 14a which generally encircles openings 186 and 188 to channel 178. Xenograft 182 is tied with a suture knot 190 after buttressing and affixing the capsule to the body member.

Figure 15:
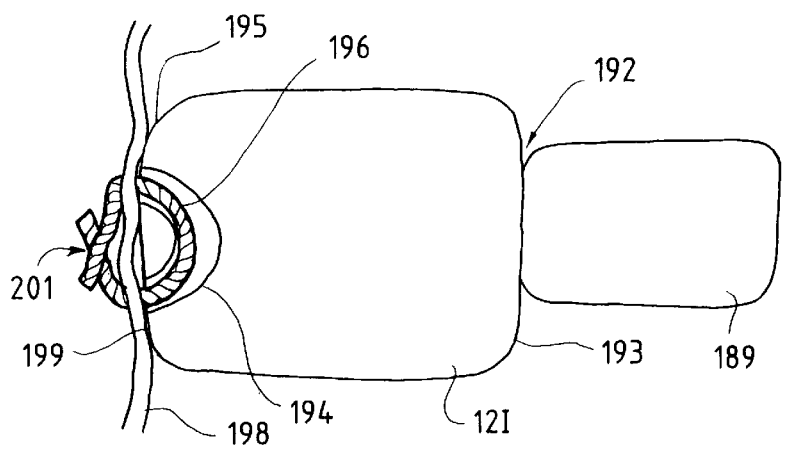
FIG. 15 is a diagrammatic/symbolic representation of a surgically implantable prosthesis in accordance with the present invention in which the prosthesis is moored to connective tissue on one side and to bone on the other.
Figure 15A:
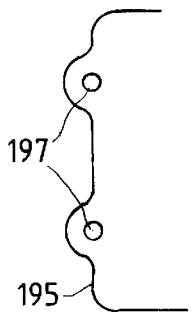
FIG. 15a is a diagrammatic/symbolic representation of another embodiment of the invention in which eyelets are provided for attachment of suture or ligamentous means.

FIG. 15 illustrates yet another embodiment of the invention. In this embodiment, a body member 12I is shown attached to a portion of native bone 189 by a cement such as Norian® paste which enables and promotes ingrowth over time of the bone to a bone ingrowth surface at 192 on side 193 of the body member. A looping channel 194 is provided opening on side 195 of the body member. Ligamentous means in the form of a strip of ingrowth receptive porous woven fabric 196 lies in the channel and is sutured at 201 under tension to adjacent connective tissue at 198, in this case, capsule. A tissue ingrowth surface 192 covers the entire surface of side 193 of the body member which is thus moored by bone growth at one end to bone 189. At the other end, the ingrowth surface 199 of implant side 195 is buttressed and affixed to capsule 198, allowing natural ingrowth to surface 199, overtime. In FIG. 15a, an alternate arrangement on side 195 of the body member is illustrated in which eyelets 197 are provided. Suture or ligamentous means are passed through these eyelets to obtain buttressing/affixation like that achieved with xenograft 182 in channel 17B of FIG. 15.

Figure 16:
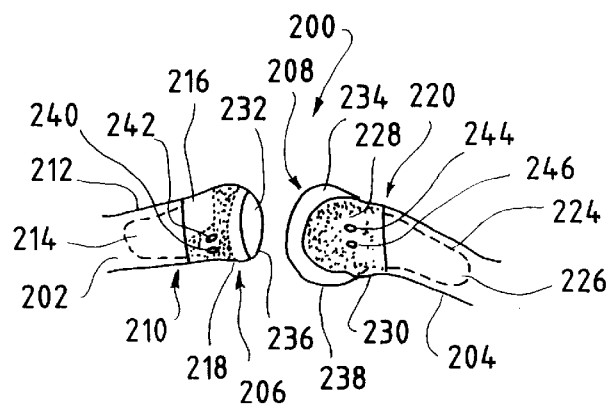
FIGS. 16 and 17 illustrate a two part prosthesis in accordance with the present invention employed at the metacarpo-phalangeal joint.
Figure 17:
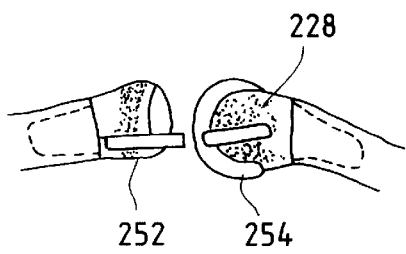

Yet another preferred embodiment of the present invention is illustrated in FIGS. 16 and 17, in which a metacarpophalangeal joint 200 is shown, with all capsule and ligaments removed for purposes of illustration. In practice, the capsule and ligaments will be surgically stripped from native bone and preserved while the portion of bone to be replaced (articular surface) is surgically removed to enable the prosthesis to be put in place. The preserved capsule and ligaments are surgically attached to the implant after the implant stem has been positioned and secured within the native metacarpal bone canal. Joint 200, as illustrated, includes a proximal phalanx 202 and a metacarpal head 204 juxtaposed so that their respective articular surfaces 206 and 208 are opposite one another.

Proximal phalanx 202 is prepared by removing the articular surface base of the native phalanx, cutting straight across just proximally to the articular surface along line 210 and drilling the exposed bone medulary canal of the phalanx to form a longitudinal bone shaft cavity 212 for receiving the stem 214 of body member 216. In this embodiment, the body member 216 is partially covered with an ingrowth surface 218. Thus, the stem of the body member is press-fit into bone shaft cavity 212 and, over time, bone ingrowth proceeds between the native bone surface of this proximal phalanx medulary cavity and the exterior bone ingrowth surface of the stem 214 of the body member.

Metacarpal head 204 is prepared in the same way by cutting across the native distal metacarpal bone neck along line 220 and drilling the exposed canal of the metacarpal bone shaft to form a longitudinal medulary cavity 224 for receiving the stem 226 of body member 228. Again, the body member stem 228 is covered with an ingrowth surface 230, and the stem of the body member is press-fit in the exposed medulary bone cavity, so that bone ingrowth proceeds over time to permanently fix the body member in place. Alternatively, the stems may be cemented using traditional methyl methacrylate bone cement.

Finally, articular heads and bases 232 and 234 having respective hard, smooth outer surfaces 236 and 238 are provided. These articular heads and bases are molded and permanently fixed to the implant by conventional means, preferably during manufacture of the implant. The implant articular surfaces are positioned on the exposed surfaces of the body members so that once surgically implanted, the articulation between the opposing metacarpal head and the base of the phalanx can be obtained as in the native joint.

Channels 240 and 242 pass through body member 216 and channels 244 and 246 pass through body member 218 to accept mooring means (e.g., suture or tendon) for mooring the native radial and ulnar collateral ligaments of the metacarpal phalangeal joint to the implant ingrowth site receptive zones 218 at 228. As mentioned above, these ingrowth sites on the implant generally correspond to the native anatomical sites of collateral ligament attachment. As shown in FIG. 17, ligamentous means 252 and 254 are inserted into these mooring channels and used to draw, buttress, and affix the native collateral ligaments to the exposed ingrowth surface (s) of the implant metacarpal head and the proximal phalanx, respectively. The collateral ligaments and their attached mooring means thus serve to stabilize the joint while permanent ingrowth of the collateral ligaments into the implant ingrowth zones proceeds naturally over time.

Figure 18:
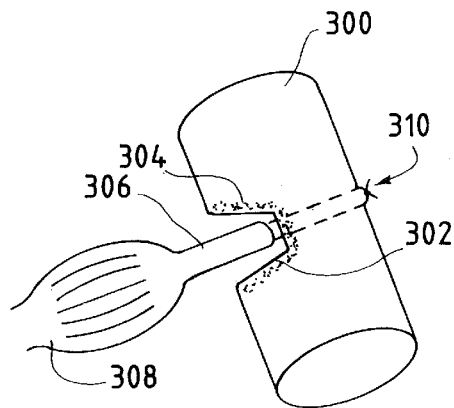
FIG. 18 is a diagrammatic/symbolic representation of a surgically implantable prosthesis in accordance with the present invention in which a tendon is moored to synthetic bone with a partial depth channel and ingrowth stationing site.

Turning now to FIG. 18, a portion of a bone segmental replacement prosthesis comprising a synthetic bone 300 is shown. The synthetic bone has a cavity 302 which passes at an angle to its longitudinal axis. This cavity is provided with an ingrowth surface 304. Thus, tendon 306 (attached to muscle 308) is drawn into cavity 302 under tension. Mooring suture channels 309 are provided. Mooring means (suture) 305, attached to tendon 306, moors the tendon to ingrowth surface 304. The mooring sutures are then tied down, under tension, at site 310, the opposite implant surface. Thus, the tendon is moored and affixed while ingrowth proceeds naturally over time.

It should be recognized that, while the invention has been described in relation to preferred embodiments thereof, those skilled in the art may develop a wide variety of structural details without departing from the principles of the present invention. Accordingly, the appended claims are to be construed to cover all equivalents falling within the scope and spirit of the invention.

What I claim is:

1. A surgically implantable bone and bone joint prosthesis comprising:
   a body member;
   means for direct immediate attachment of the body member to adjacent connective tissue; and
   at least one connective tissue ingrowth receptive stationing site on or in the body member for delayed ingrowth adhesion naturally over time.

2. The surgically implantable bone and bone joint prosthesis of claim 1 in which the body member is made from a bio-compatible, medically inert material chosen from the group consisting of ceramic, titanium, stainless steel alloy, non-ceramic substrate with a ceramic or other bio-compatible, medically inert coating, and open-celled lattice tantalum metal-carbon foam composite material.

3. The surgically implantable bone and bone joint prosthesis of claim 1 in which the body member comprises a non-ceramic substrate with a ceramic or other bio-compatible, medically inert coating.

4. The surgically implantable bone and bone joint prosthesis of claim 1 in which the body member comprises a single component contoured to resemble the shape of the bone or portion of a bone that is to be replaced by the prosthesis.

5. The surgically implantable bone and bone joint prosthesis of claim 1 in which the prosthesis comprises at least two body members contoured to resemble the shapes of the bones, bone joints or portions of a bone or bones that are to be replaced by the prosthesis.

6. The surgically implantable bone and bone joint prosthesis of claim 1 in which mooring means are provided to draw connective tissue to the ingrowth surface of the stationing site to achieve buttressing and affixation of the body member to adjacent connective tissue.

7. The surgically implantable bone and bone joint prosthesis of claim 1 in which adhesive with impregnated bone or connective tissue ingrowth factors is applied to the ingrowth surface of the stationing site.

8. The surgically implantable bone and bone joint prosthesis of claim 6 in which the mooring means are chosen from the group consisting of sutures, anchors, interference screws, and medical staples.

9. The surgically implantable bone and bone joint prosthesis of claim 6 in which the mooring means are ligamentous means.

10. The surgically implantable bone and bone joint prosthesis of claim 9 in which the ligamentous means are chosen from the group consisting of local tissue, autografts, allografts, xenografts, synthetic grafts, and porous woven fabric which is tissue ingrowth receptive.

11. A surgically implantable bone and bone joint prosthesis comprising:
   a body member;
   means for direct immediate attachment of the body member to adjacent connective tissue;
   at least one connective tissue ingrowth receptive stationing site on or in the body member for delayed ingrowth adhesion naturally over time; and
   ligamentous means to draw connective tissue to the ingrowth surface of the stationing site to achieve buttressing and affixation of the body member to adjacent connective tissue, the ligamentous means being chosen from the group consisting of capsular strips, bone-ligament-bone graft, and tendon.

12. The surgically implantable bone and bone joint prosthesis of claim 9 in which the ligamentous means are bone-ligament-bone grafts in which the volume of the bone portions is enhanced with synthetic bone paste;
   bone-ligament-bone grafts to draw connective tissue to the ingrowth surface of the stationing site to achieve buttressing and affixation of the body member to adjacent connective tissue.

13. The surgically implantable bone and bone joint prosthesis of claim 9 in which the ligamentous means are pairs of bone-ligament grafts with the bone portions touching.

14. The surgically implantable bone and bone joint prosthesis of claim 9 in which the ligamentous means are affixed to adjacent native connective tissue.

15. The surgically implantable bone and bone joint prosthesis of claim 13 in which the ligamentous means are affixed to adjacent bone.

16. The surgically implantable bone and bone joint prosthesis of claim 1 in which the ingrowth receptive zones emulate the surfaces of native bone where native connective tissue attaches in situ.

17. The surgically implantable bone and bone joint prosthesis of claim 1 in which the ingrowth receptive zones are located at locations on the body member corresponding generally to the areas where connective tissue naturally attaches in vivo to the bones or portions of bones which are to be replaced by the prosthesis.

18. The surgically implantable bone and bone joint prosthesis of claim 1 in which the ingrowth receptive zones are of a size and shape corresponding generally to the size and shape of the metaphyseal or diaphyseal areas of bone to which the connective tissue is attached in vivo to the bones or portions of bones which are to be replaced by the prostheses.

19. A surgically implantable bone and bone joint prosthesis comprising:
   a body member;
   means for direct immediate attachment of the body member to adjacent connective tissue; and
   at least one connective tissue ingrowth receptive stationing site on or in the body member for delayed ingrowth adhesion naturally over time, the ingrowth receptive zones being treated with humeral growth factors to further induce ingrowth.

20. The surgically implantable bone and bone joint prosthesis of claim 1 in which the ingrowth receptive zones are treated with biologic adhesives.

21. The surgically implantable bone and bone joint prosthesis of claim 1 in which the body member includes a pair of generally parallel channels through which mooring means comprising ligamentous means or suture can be passed to draw connective tissue to the ingrowth surface of stationing sites adjacent to the channel openings.

22. The surgically implantable bone and bone joint prosthesis of claim 1 in which at least one body member includes a channel which loops into and back out of the surface of the body member so that mooring means comprising ligamentous means or suture can be passed through this looping channel to draw connective tissue to the ingrowth surface of stationing sites adjacent to the channel openings.

23. The surgically implantable bone and bone joint prosthesis of claim 1 in which the body member includes at least one channel with at least one stationing site at least one of the channel openings so that mooring means in the form of suture or ligamentous means may be passed therethrough to draw connective tissue to the ingrowth receptive surface of the stationing site.

24. The surgically implantable bone and bone joint prosthesis of claim 23 in which the ligamentous means or suture is physically anchored in the channel.

25. The surgically implantable bone and bone joint prosthesis of claim 24 in which the ligamentous means or suture is anchored in the channel by attaching the suture or ligamentous means to the channel wall with adhesive, anchors, or interference screws.

26. A surgically implantable bone and bone joint prosthesis comprising:
   a body member and means for direct immediate attachment of the body member to adjacent connective tissue, the body member including at least one channel with at least one connective tissue ingrowth receptive stationing site for delayed ingrowth adhesion naturally over time at least one of the channel openings so that mooring means in the form of suture or ligamentous means may be passed therethrough to draw connective tissue to the ingrowth receptive surface of the stationing site; and ingrowth receptive zones on the walls of the channel to secure the ligamentous means to the prosthesis over time.

27. The surgically implantable bone and bone joint prosthesis of claim 26 in which the ligamentous means comprise bone-ligament-bone grafts anchored in the channels.

28. The surgically implantable bone and bone joint prosthesis of claim 26 in which the anchored bone of two grafts at opposite ends of a channel touch whereby, over time the touching bones of the bone-ligament-grafts will grow together producing a single bone-ligament-bone-ligament ligamentous means mooring the body member in place.

29. The surgically implantable bone and bone joint prosthesis of claim 6 in which the mooring means are secured to the periphery of the body member.

30. A surgically implantable bone and bone joint prosthesis comprising:
   a body member;
   means for direct immediate attachment of the body member to adjacent connective tissue;
   at least one connective tissue ingrowth receptive stationing site on or in the body member for delayed ingrowth adhesion naturally over time; and mooring means are provided to draw connective tissue to the ingrowth surface of the stationing site to achieve buttressing and affixation of the body member to adjacent connective tissue, wherein the mooring means are secured to the periphery of the body member by way of eyelets formed in the surface of the body member.

31. The surgically implantable bone and bone joint prosthesis of claim 1 in which the body member is stabilized by suspending it on suture or ligamentous means along at least two crisscrossing axes.

32. The surgically implantable bone and bone joint prosthesis of claim 31 in which the axes are substantially perpendicular.

33. A surgically implantable bone and bone joint prosthesis comprising:

a body member;

at least one ingrowth receptive stationing site on or in the body member for delayed ingrowth adhesion naturally over time; and mooring means for directly attaching the body member to adjacent connective tissue while drawing the connective tissue to the ingrowth surface to achieve buttressing and affixation of the body member to adjacent connective tissue.

34. The surgically implantable bone and bone joint prosthesis of claim 33 in which the prosthesis comprises at least two body members contoured to resemble the shapes of the bones, bone joints or portions of a bone or bones that are to be replaced by the prosthesis.

35. The surgically implantable bone and bone joint prosthesis of claim 33 in which mooring means are provided to draw connective tissue to the ingrowth surface of the stationing site to achieve buttressing and affixation of the body member adjacent to connective tissue while ingrowth proceeds over time.

36. A surgically implantable bone and bone joint prosthesis comprising:

a body member;

at least one ingrowth receptive zone on or in the body member for delayed ingrowth adhesion naturally over time; and ligamentous means for directly attaching the body member to adjacent connective tissue while drawing the connective tissue to the ingrowth surface to achieve buttressing and affixation of the body member to adjacent connective tissue.

37. The surgically implantable bone and bone joint prosthesis of claim 36 in which the ligamentous means are chosen from the group consisting of local tissue, autografts, allografts, xenografts, synthetic grafts, and porous woven fabric which is tissue ingrowth receptive.

38. A surgically implantable bone and bone joint prosthesis comprising:

a body member;

at least one ingrowth receptive zone on or in the body member for delayed ingrowth adhesion naturally over time; and ligamentous means chosen from the group consisting of capsular strips, bone-ligament-bone graft, and tendon for directly attaching the body member to adjacent connective tissue while drawing the connective tissue to the ingrowth surface to achieve buttressing and affixation of the body member to adjacent connective tissue.

39. The surgically implantable bone and bone joint prosthesis of claim 36 in which the ligamentous means are affixed to adjacent native connective tissue.

40. The surgically implantable bone and bone joint prosthesis of claim 36 in which the ligamentous means are affixed to adjacent bone.

41. A surgically implantable bone and bone joint prosthesis comprising:

a body member;

means for direct immediate attachment of the body member to adjacent connective tissue;

at least one connective tissue ingrowth receptive stationing site on or in the body member for delayed ingrowth adhesion naturally over time; and bone-ligament-bone grafts to draw connective tissue to the ingrowth surface of the stationing site to achieve buttressing and affixation of the body member to adjacent connective tissue.

42. A surgically implantable bone and bone joint prosthesis comprising:

a body member;

means for direct immediate attachment of the body member to adjacent connective tissue;

at least one connective tissue ingrowth receptive stationing site on or in the body member for delayed ingrowth adhesion naturally over time;

bone-ligament-bone grafts to draw connective tissue to the ingrowth surface of the stationing site to achieve buttressing and affixation of the body member to adjacent connective tissue; and pairs of bone-ligament grafts with the bone portions touching.

\* \* \* \* \*